United States Patent [19]

Christensen et al.

[11] Patent Number: Plant 5,399

[45] Date of Patent: Jan. 29, 1985

[54] ROSE PLANT CV. AROJECHS

[75] Inventors: Jack E. Christensen; Herbert C. Swim, both of Ontario, Canada

[73] Assignee: Armstrong Nurseries, Inc., Ontario, Canada

[21] Appl. No.: 503,045

[22] Filed: Jun. 10, 1983

[51] Int. Cl.[3] ..... A01H 5/00

[52] U.S. Cl. ..... Plt./22

[58] Field of Search ..... Plt./22

*Primary Examiner*—Robert E. Bagwill

*Attorney, Agent, or Firm*—Synnestvedt & Lechner

[57] ABSTRACT

A new variety of rose plant of the hybrid Floribunda class, being a hardy, tall outdoor seedling of the bush type, grown mainly for garden decoration and which displays a unique multicoloration which is basically yellow, blushing to orange and finishing red. The flowers are produced in abundance, nearly continuously and are well distributed over the tall bush.

1 Drawing Figure

This invention relates to a new variety of Hybrid Floribunda rose. The plant is a hardy, tall, bushy outdoor seedling grown mainly for garden decoration. The flowers of the Arojechs rose plant have a unique multicoloration which is basically yellow, blushing to orange and finishing red. The flowers are produced in abundance and nearly continuously and are well distributed over the tall bush. Its abundant glossy foliage covers the entire bush. The variety continues to flower despite the presence of maturing hips. It shows a high level of disease-resistance and over-all vigor.

It was hybridized by crossing Jack O'Lantern (U.S. Plant Pat. No. 1,985) as the seed parent with Zorina (U.S. Plant Pat. No. 2,321) as its pollen parent. The plant was hybridized in Ontario, Calif. by Herbert C. Swim and Jack E. Christensen. The new variety holds its distinguishing characteristics through succeeding propagations by cuttings and by budding.

This rose cultivar may most readily be distinguished from its seed parent, Jack O'Lantern, by the following combination of characteristics:

Whereas flowers of Jack O'Lantern have a diameter of about 4 to 4½ inches, the new rose bears flowers of significantly smaller diameter (2 to 3 inch) essentially as more fully described below, and as illustrated herein.

The new cultivar bears flowers in large clusters, whereas Jack O'Lantern usually bears one flower per stem.

Jack O'Lantern is classified as a Hybrid Tea, whereas the new rose is classified as a Floribunda.

Whereas Jack O'Lantern is designated more for greenhouse cut flower usage, the new cultivar Arojechs is designated only for use in garden decoration.

This new rose cultivar may be distinguished from its pollen parent, Zorina, by the following combination of characteristics:

Whereas the new cultivar bears flowers of a multicoloration essentially as described and illustrated herein, Zorina bears flowers of a relatively uniform orange-red coloration.

The new rose is useful only in garden decoration, whereas Zorina is predominately used in the greenhouse cut flower industry.

Whereas the new seedling produces a tall, upright bushy plant, the mature plant of Zorina is of a significantly shorter and more rounded habit.

The accompanying drawing illustrates the plant in color, and shows the flowering thereof from bud to full bloom.

Throughout this specification, color names beginning with a small letter signify that the name of that color, as used in common speech, is aptly descriptive. Color names beginning with a capital letter designate values based upon The R.H.S. Colour Chart published by The Royal Horticultural Society of London, England.

FLOWER

The plant bears its flowers usually several to a stem in irregular rounded clusters, on normal medium length stems. It blooms abundantly outdoors, and nearly continuously during the growing season even in the presence of a heavy seed set.

BUD

The peduncle is of short to average length and of average caliper, erect and stiff, moderately rough, with numerous stipitate glands and some small prickles.

Before the calyx breaks, the bud is of small to medium size (for floribunda roses), of medium length, pointed and ovoid in form, and with some stipitate glands on the surface of the bud. There are usually slender foliaceous parts extending beyond the tip of the bud equal to one-half or more of its length.

As the calyx breaks, the color is between Yellow 12A and Yellow-Orange 14C; areas exposed to the sun are blushed to between Orange-Red 34B and Red 46C. The inner surface of the sepals carries a fine, wooly tomentum. Margins are lined with stipitate glands.

As the first petal opens, the bud is of average size for floribunda roses, of medium length, pointed and ovoid. On the outer surface of the petal, the basal area is between Yellow 12B and Yellow 13C and suffuses to between Yellow 11C and Yellow 13D approaching the petal edge. Areas exposed to sunlight blush as deeply as between Red 34C and Red 46C. On the inner surface of the petal, the basal area is between Yellow 12A and Yellow 13B and suffuses to between Yellow 11B and Yellow 12C approaching the petal edge. Areas exposed to sunlight blush as deeply as between Red 34A and Red 46C. The bud opens up well and is not retarded or prevented from opening or destroyed by cold, hot, wet or dry weather.

BLOOM

When fully open, the bloom is of small to average size, being from 2 to 3 inches in diameter. The petalage is double, with from 22 to 28 petals, plus from 0 to 3 petaloids arranged regularly. In form, the bloom is high centered at first and becoming cupped; the petals at first being cupped with tips reflexed outward, becoming later at maturity more loosely cupped, with tips reflexed outward.

The petals are thick, with inside slightly satiny and outside shiny to satiny. The outside petals are round to broadly obovate, with a rounded apex. Intermediate petals are broadly obovate, and with apex rounded. Inside petals are narrowly obovate with rounded apex. The colors may be modified by being bordered or blotched, shaded or washed or tinted with other colors.

The description which follows is of the color values noted in a flower newly opened in the month of August. The plant had been grown outdoors in Ontario, Calif.

On the outer surface of the outside petals, the basal area is between Yellow 13B and Yellow-Orange 14C suffusing to between Yellow 11C and Yellow 13D approaching the petal edge. Areas exposed to sunlight blush as deeply as between Orange-Red 34C and Red 46C. On the inside surface of the outside petals, the basal area is of a coloration between Yellow 13A and Yellow-Orange 14C suffusing to between Yellow 11B and Yellow 12C approaching the petal edge; areas exposed to sunlight blush as deeply as between Red 34A and Red 46C.

The outside surface of the intermediate petals have the same coloration as the outer surface of the outside petals but with much less blushing. The inside surface of intermediate petals have the same coloration as the inside surface of the outer petals but with less intense blushing. The outside surface of inner petals have the same coloration as the outer surface of the outside petals but without any blushing. The inside surface of inner petals have the same coloration as the inside surface of the outer petals but with very little blushing.

The following description is of a rose that was open for three days. It has been grown outdoors in the month of August, in Ontario, Calif.

The outside surface of outside petals are between yellow 9D and Yellow 10D in color with areas exposed to sunlight blushing as deeply as between Red 35A and Red 47C. The outside surface of the inside petals are of the same coloration but without blushing. The inside surfaces of the outside and inside petals are of the same coloration, namely, between Yellow 10C and Yellow 9D with areas exposed to sunlight blushing as deeply as between Red 45B and Red 46C.

The general color effect: the newly opened flower has a central coloration of between Yellow 13A and Yellow-Orange 14C, blushing as deeply as between Red 34A and Red 46C on the outer petals. After being three days open, the predominant coloration is between Red 45B and Red 46C with between Yellow 9D and Yellow 10C in the depth of the flower. The petals drop off cleanly, and are not particularly affected by cold, hot, wet or dry weather.

The flower on the bush in the garden persists for from 3 to 4 days in the month of August, in the locality named. Cut roses grown outdoors and kept at living-room temperatures will last from 4 to 5 days in the month of August.

REPRODUCTIVE ORGANS

There are a few to an average number of stamens, arranged regularly about the pistils.

The filaments are of medium-length and most are with anthers.

Anthers are medium in size, all opening approximately at once. The color, when immature, is near Yellow-Orange 17B in color. The color, when mature, is near Greyed-Orange 166A.

There is a moderate to abundant amount of pollen, which is near Yellow-Orange 17D in coloration.

There are a few to an average number of pistils, approximately 35 in number.

The styles are moderately uneven, of average length, of thin to average caliper and loosely bunched.

The color of the stigma is near Yellow 4C.

Most of the ovaries are usually enclosed in the calyx.

Immature hips are moderately rough and short and globular in shape and near Yellow-Green 151A in color. Hip walls are thick and fleshy.

The sepals fall soon.

There are an average number of seeds, from 8 to 15 in number, and usually of small to medium-size.

FOLIAGE

The compound leaves usually comprise from three to five and sometimes seven leaflets. They are very abundant, of medium size, heavy to somewhat leathery, and glossy. The leaflets are oval in shape, with apex acute, base acute and margin simply serrate.

On its upper surface, the mature foliage is between Green 139A and 136A. The under surface is between Yellow-Green 147B and Greyed-Green 194A.

The upper and under surfaces of the young foliage are between Greyed-Purple 187A and Greyed-Purple 183A in color.

The rachis is of average size, the upper side being grooved, with many stipitate glands on the edges. The under side is moderately prickly with stipitate glands.

The stipules are of medium-length, moderately narrow and with medium-length points turning out at an angle of more than 45°.

The plant displays a more than average resistance to mildew and blackspot, when compared to other varieties now in commerce grown under Ontario, Calif. conditions.

GROWTH

The plant is upright and bushy in habit and much branched. It displays a very vigorous growth. Canes are of medium to heavy caliper.

The main stems are between Yellow-Green 146A to Green 139C in coloration and are sometimes blotched irregularly with near Greyed-Orange 177A. They bear a few large prickles, which are of medium-length, almost straight to hooked slightly downward, with a medium-length, broad base. Their color is between Greyed-Orange 177C and Greyed-Orange 175B. There are no small prickles and no hairs.

The branches are between Yellow-Green 146A and Green 139B in color and the sunside sometimes blushes near Greyed-Orange 176A. They carry several large prickles, which are of medium-length, almost straight to hooked slightly downward and with a medium-length, broad base. They are near Greyed-Orange 175B in color. There are several near Greyed-Orange 175B small prickles and no hairs.

New shoots are near Yellow-Green 146D in color and heavily washed with near Greyed-Purple 183A. They bear several medium-length large prickles, which are almost straight to hooked slightly downward, with a medium-length, moderately broad base. They are near Greyed-Purple 183A in color. There are several near Greyed-Purple 183A small prickles and a few near Greyed-Purple 183A hairs.

We claim:

1. A new and distinct variety of Floribunda rose plant cv. Arojechs, substantially as herein shown and described, and being especially characterized in the unique multicoloration of the flowers which is basically yellow blushing to orange and finishing red; in the abundance of its glossy foliage, which covers the entire bush; in the abundance and nearly continuous production of flowers distributed well over the tall bush, in its ability to continue to flower despite the presence of maturing hips, and in its high level of disease resistance and overall vigor.

* * * * *

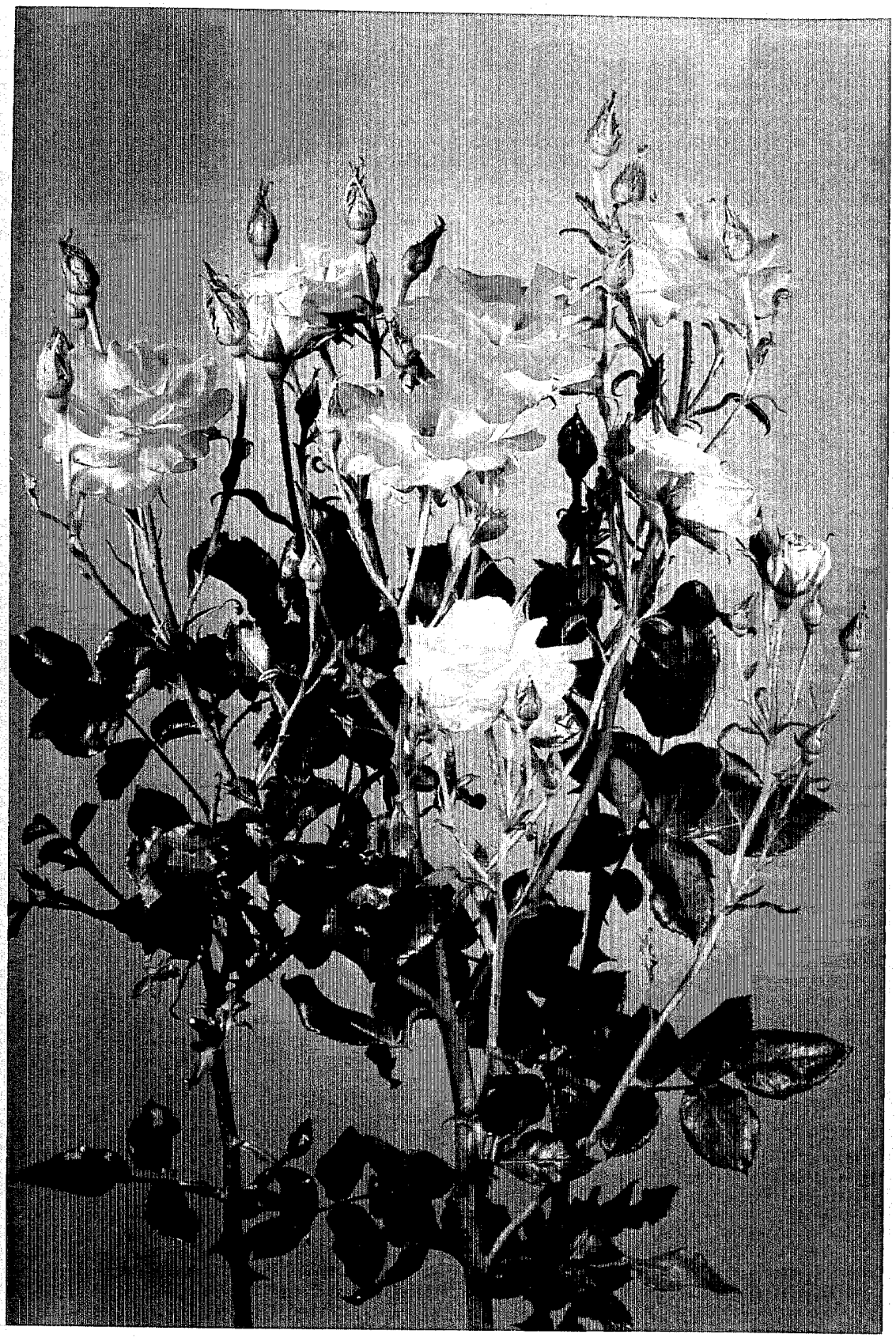

UNITED STATES PATENT AND TRADEMARK OFFICE

CERTIFICATE OF CORRECTION

PATENT NO. : PP 5399

DATED : January 29, 1985

INVENTOR(S) : Jack E. Christensen

It is certified that error appears in the above-identified patent and that said Letters Patent is hereby corrected as shown below:

On the title page;

Bibliographic Data, INID Code No. [73]: change "Armstrong Nurseries, Inc., Ontario, Canada" to --Armstrong Nurseries, Inc., Ontario, California--.

Signed and Sealed this

*Thirteenth* Day of *August 1985*

[SEAL]

*Attest:*

DONALD J. QUIGG

*Attesting Officer* *Acting Commissioner of Patents and Trademarks*